United States Patent
Enscore

(10) Patent No.: US 12,370,149 B1
(45) Date of Patent: Jul. 29, 2025

(54) TRANSDERMAL CANNABIDIOL DELIVERY DEVICE

(71) Applicant: ZHI Technologies, Inc., Fort Lauderdale, FL (US)

(72) Inventor: David Enscore, Fort Lauderdale, FL (US)

(73) Assignee: ZHI Technologies, Inc., Fort Lauderdale, FL (US)

( * ) Notice: Subject to any disclaimer, the term of this patent is extended or adjusted under 35 U.S.C. 154(b) by 0 days.

(21) Appl. No.: 18/659,750

(22) Filed: May 9, 2024

(51) Int. Cl.
*A61K 9/70* (2006.01)
*A61K 31/00* (2006.01)

(52) U.S. Cl.
CPC .......... *A61K 9/7053* (2013.01); *A61K 31/658* (2023.05)

(58) Field of Classification Search
None
See application file for complete search history.

(56) References Cited

U.S. PATENT DOCUMENTS

| | | | |
|---|---|---|---|
| 6,348,210 B1 * | 2/2002 | Gale | A61K 9/7053 424/448 |
| 9,962,340 B2 | 5/2018 | Weimann | |
| 10,588,869 B2 | 3/2020 | Weimann | |
| 10,799,545 B2 | 10/2020 | Weimann | |
| 11,285,117 B2 | 3/2022 | Weimann | |
| 2010/0290998 A1 * | 11/2010 | Jones | A61P 9/10 424/9.1 |
| 2020/0188316 A1 | 6/2020 | Bender | |
| 2021/0228497 A1 | 7/2021 | Weimann | |

OTHER PUBLICATIONS

Haus, F., et al., Biodegradation 11: 365-369 (2000). (Year: 2000).*

* cited by examiner

*Primary Examiner* — David J Blanchard
*Assistant Examiner* — Daniel F Coughlin
(74) *Attorney, Agent, or Firm* — Rothwell, Figg, Ernst & Manbeck, P.C.

(57) ABSTRACT

Transdermal delivery devices (TDDs) that provide an easy-to-use method of delivering a consistent, steady dose of cannabidiol (CBD) are shown and described herein. The TDDs include a backing layer coated with a mixture of CBD, a polyisobutene adhesive, and plasticizer. Methods of making and using the same are also described.

26 Claims, 1 Drawing Sheet

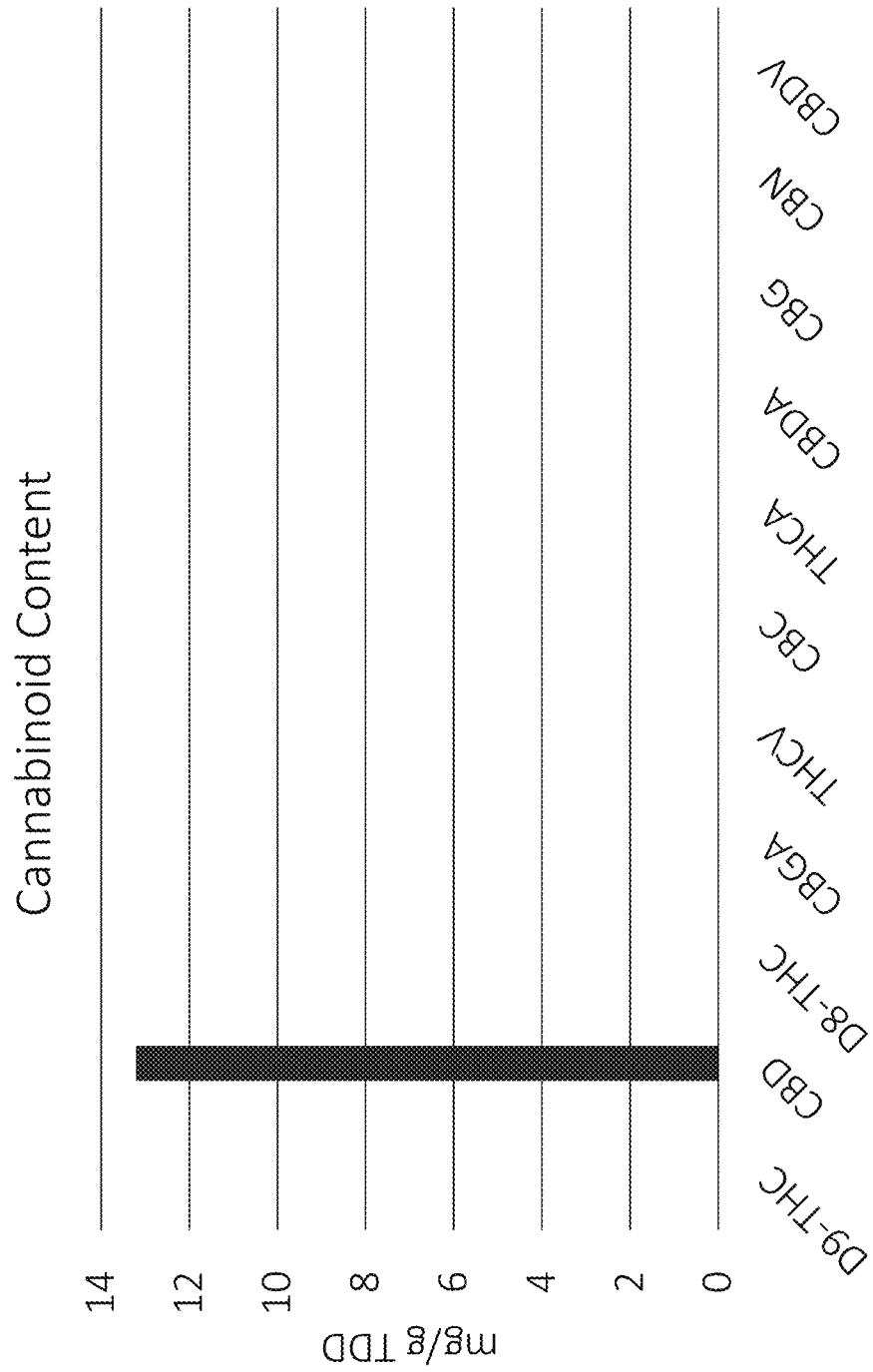

TRANSDERMAL CANNABIDIOL DELIVERY DEVICE

TECHNICAL FIELD

The present disclosure relates to a medical device for the transdermal delivery of cannabidiol (CBD).

BACKGROUND

CBD (CAS Registry No. 13956-29-1) and tetrahydrocannabinolic acid are the principal pharmacoactive components of *Cannabis sativa, Cannabis indica,* & *Cannabis ruderalis*. While transdermal delivery has been attempted, transdermal delivery of CBD remains challenging due to the nature of human skin and the properties of CBD itself.

U.S. Pat. No. 9,962,340 to Weimann reports transdermal CBD delivery reservoir-patch comprising a hydrophilic, microporous membrane enclosing a polar liquid loaded with CBD. The highest total CBD flux that Weimann reports achieving across 24 hours is ~230 µg/cm$^2$.

U.S. Pat. No. 11,285,117 to Weimann reports transdermal delivery patches comprising polyisobutylene (PIB) adhesives for delivering CBD and additional cannabinoids across the skin from a liquid saturated PIB matrix. The highest total CBD flux reported in this patent across 24 hours is ~230 µg/cm$^2$.

U.S. Published Application No. 2021/0228497 to Weimann reports transdermal delivery patches comprising a CBD-saturated PIB matrix. The highest total CBD flux reported in this published application across 24 hours is ~100 µg/cm$^2$.

Accordingly, as a result of the lipophilic properties of CBD, its flux through human skin is a limiting factor in dosing and delivery. There remains an unmet need for products and methods that can overcome these limitations to increase CBD flux.

SUMMARY

Disclosed herein are transdermal delivery devices (TDDs) comprising a backing layer and a matrix. The matrix comprises polyisobutylene (PIB) adhesive, a plasticizer (e.g., an oil), and cannabidiol (CBD). In certain embodiments, the matrix comprises at least threefold more CBD than a maximum concentration of CBD that dissolves in the oil, the PIB adhesive has an average molecular weight greater than 100 kDa, and the backing layer is inert to the matrix.

In certain embodiments, the plasticizer is a mineral oil with a kinematic viscosity of about 5-30 cSt at 40° C., and about 10% (w/w) to about 30% (w/w) of the mass of the matrix is the mineral oil.

In certain embodiments, the PIB comprises polymers with a molecular weight from about 800 kDa to about 4 MDa and polymers with a molecular weight from about 25 kDa to about 65 kDa in a ratio of about 1:2 to about 2:1.

In certain embodiments, about 15-25% (w/w) of the mass of the matrix is CBD, about 55-66% (w/w) of the mass of the matrix is PIB, and about 17-28% (w/w) of the mass of the matrix is a mineral oil with a kinematic viscosity of about 10.8-13.6 cSt at 40° C. In certain embodiments, about 16-17% (w/w) of the matrix is CBD. In certain embodiments, the matrix comprises at least fourfold more CBD than the saturation concentration for CBD in the oil.

In certain embodiments, the TDD further comprises a 1.0-5.0 mm thick polyethylene terephthalate (PET) film coated with a release agent and/or a 1.0-5.0 mm thick low density polyethylene (LDPE) film.

In certain embodiments, the TDD is configured to deliver at least 0.5 mg/cm$^2$ of CBD across skin of a human subject after adherence of the TDD to the skin for at least 24 hours. In certain embodiments, the TDD is configured to deliver at least 0.65 mg/cm$^2$ of CBD across skin of a human subject after adherence of the TDD to the skin for at least 24 hours. In certain embodiments, the TDD is configured to deliver at least 50% (w/w) of the CBD through a subject's skin after adherence of the TDD to the skin for at least 12 hours. In certain embodiments, the TDD is configured to deliver at least 70% (w/w) of the CBD through a subject's skin after adherence of the TDD to the skin for at least 24 hours.

Also disclosed herein are methods of delivering CBD to a subject comprising adhering the TDD of claim 1 to skin of the subject. In certain embodiments, the TDD delivers CBD at a transdermal flux of at least 0.6 mg/cm$^2$ per 24 hours to the subject. In certain embodiments, the TDD adheres to skin of the subject for at least 8 hours.

Also disclosed herein are method of treating a subject suffering from a variety of disorders (e.g., seizures), comprising adhering the TDD to skin of the subject. The U.S. Food and Drug Administration (FDA) has approved CBD for treatment of seizures/epilepsy (EPIDIOLEX®). Similarly, methods are disclosed herein for enhancing an analgesic effect in a subject in need of pain relief comprising adhering the TDD to skin of the subject, wherein the subject has been, is, or will be administered an analgesic agent. The analgesic and anti-inflammatory effects of CBD has been demonstrated in various models, including neuropathic pain, inflammatory pain, osteoarthritis and others including hyperalgesia or allodynia, as well as the production of pro and anti-inflammatory cytokines. Mlost J, Bryk M, Starowicz K. Cannabidiol for Pain Treatment: Focus on Pharmacology and Mechanism of Action. Int J Mol Sci. 2020 Nov. 23; 21(22):8870. doi: 10.3390/ijms21228870. PMID: 33238607; PMCID: PMC7700528.

Finally, methods of making a pharmaceutical matrix are disclosed herein, in which one mixes about 35 to about 70 weight parts of PIB adhesive having an average molecular weight greater than 100 kDa with about 15 to about 50 parts by weight of an oil and at least 15 parts by weight of CBD. In certain embodiments, the method comprises a first mixing step of mixing the CBD with the oil in an organic solvent to obtain a first mixture, followed by a second mixing step of mixing the first mixture with the PIB adhesive and stirring. In certain embodiments the first mixing step has a higher stir rate than the second mixing step.

BRIEF DESCRIPTION OF THE DRAWINGS

FIG. 1 shows the concentration of each of a series of cannabinoids per 234.8 mg TDD. The limit of detection for each cannabinoid assayed was 0.002%. D9-THC=delta-9-tetrahydrocannabinol. THCA=tetrahydrocannabinolic acid. CBDA=cannabidiolic acid. D8-THC=delta-9-tetrahydrocannabinol. CBG=cannabigerol. CBGA=cannabigerolic acid. CBN=cannabinol. THCV=tetrahydrocannabivarin. CBDV=cannabidivarin. CBC=cannabichromene.

DETAILED DESCRIPTION

The present disclosure teaches how to formulate TDDs with CBD in oil and PIB adhesive that are capable of achieving >500 µg/cm$^2$ CBD flux across 24 hours. At the most fundamental level, these TDDs comprise: 1) a backing layer; and 2) a matrix. The matrix includes at least PIB adhesive, an oil, and CBD. Significantly, the matrix comprises at least threefold more CBD than a maximum concentration of CBD that dissolves in the oil, with the result that the matrix achieves a "saturated-plus-excess" state. The "saturated-plus-excess" composition has the advantage of presenting CBD to the skin in a manner so that as the CBD is absorbed into the skin, the CBD concentration in the matrix immediately proximate to the skin remains constant (as the excess dissolves into the matrix). This formulation of the TDD advantageously maintains a constant rate of delivery until the CBD is close to exhausted. The saturated-plus-excess design for the TDD achieves a more uniform CDB delivery rates than is achieved with a simple reservoir design, as well as a more efficient use of material. The PIB adhesives for use in the TDDs disclosed herein have an average molecular weight greater than 100 kDa. The backing layers for use in the TDDs disclosed herein are inert to the matrix. In certain embodiments, the TDD also comprises a release liner to protect the matrix when the TDD is not in use.

In certain embodiments, the TDDs disclosed herein are capable of delivering at least 0.50 mg/cm$^2$ (e.g., at least 0.55, at least 0.60, or at least 0.65 mg/cm$^2$) of CBD across the skin and into the bloodstream of a subject (e.g., a human) after adherence of the TDD to the skin for at least 24 hours. In certain embodiments, the TDD is capable of delivering at least 50% (w/w) of the CBD through the skin and into the bloodstream of a subject (e.g., a human) after adherence of the TDD to the skin for at least 12 hours. In certain embodiments, the TDD is capable of delivering at least 70% (w/w) of the CBD through the skin and into the bloodstream of a subject (e.g., a human) after adherence of the TDD to the skin for at least 24 hours.

Backing layers. The TDDs described herein include a backing layer. Non-limiting examples of suitable materials for the backing layer include occlusive polymeric films such as polyethylene, polyethylene terephthalate (PET), low density polyethylene (LDPE) film, and combinations thereof. The backing layer must be inert to the matrix and thick enough to withstand the stress incurred as the skin stretches and contracts during the ordinary course of animal movement, but thin enough to retain flexibility so as not to inhibit movement. In ordinary use, such backing layer films will be 0.5-8.0 mm thick, for example 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5., 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.5, 7.0, 7.5 mm or more thick. In certain embodiments, the backing layer films will be 1.0-5.0 mm thick.

Matrices. In addition to the disclosure of TDDs, matrices are also described in the present disclosure that are suitable for use in the TDDs described herein. A matrix as disclosed herein comprises a skin adhesive mixed with a therapeutically effective amount of CBD. In certain embodiments, the matrix is coated on one side of a TDD backing layer. In certain embodiments, the matrix consists of PIB, mineral oil, CBD, and n-heptane residue. In certain embodiments, the matrix consists of PIB, mineral oil, and CBD.

A matrix as disclosed herein is formulated to make it possible for the TDD to adhere to the user's skin for at least about 8 hours (e.g., 10 hours, 12 hours, 18 hours, 20 hours, 24 hours, or more) without appreciably irritating the user's skin. To that end, the matrices disclosed herein comprise a polyisobutylene (PIB) adhesive. Suitable polyisobutylene adhesives have a viscosity-average molecular weight greater than 100 kDa, for example at least 150 kDa, at least 200 kDa, at least 250 kDa, at least 300 kDa, at least 350 kDa, at least 400 kDa, at least 450 kDa, or even 500 kDa or more. Such PIB adhesives can be made by blending a quantity of PIB adhesives with viscosity average molecular weights ranging from about 30 kDa to about 70 kDa—for example from about 35 kDa to about 65 kDa, or from about 40 kDa to about 60 kDa—with a quantity of PIB adhesives having a viscosity-average molecular weight ranging from 800 kDa to 4.0 MDa for example, from about 900 kDa to about 2.0 MDa, or from about 950 kDa to about 1.1 MDa. The ratios of this low:high blend can be about 1:2 to about 2:1, for example about 1:1.1 to 1.1:1. In some embodiments, the ratio about 1:1.

PIB adhesives supply 35% (w/w) to 75% (w/w) of the mass of the matrix. In certain embodiments, PIB adhesives will supply 40% (w/w) to 70% (w/w), or even 55% (w/w) to 66% (w/w) of the mass of the matrix, for example about 60.2% (w/w), about 60.4% (w/w), about 60.6% (w/w), about 60.8% (w/w), about 61.0% (w/w), about 61.2% (w/w), about 61.4% (w/w), about 61.6% (w/w), about 61.8% (w/w), about 62.0% (w/w), about 62.2% (w/w), about 62.4% (w/w), about 62.6% (w/w), about 62.8% (w/w), about 63.0% (w/w), about 63.2% (w/w), about 63.4% (w/w), about 63.6% (w/w), about 63.8% (w/w), about 64.0% (w/w), about 64.2% (w/w), about 64.4% (w/w), about 64.6% (w/w), about 64.8% (w/w), about 65.0% (w/w), about 65.2% (w/w), about 65.4% (w/w), about 65.6% (w/w), about 65.8% (w/w), or about 66.0% (w/w).

In certain embodiments, the PIB adhesive is supplied as a solution of at least 30% (w/w) (e.g., at least 32% (w/w), at least 34% (w/w), at least 36% (w/w), at least 38% (w/w), or at least 40% (w/w)) solids solution in n-heptane.

Certain suitable PIB adhesives are sold with mineral oil incorporated, and others without mineral oil, but both sorts are useful in the matrices and TDDs of the present disclosure. If the adhesive, as supplied, contains mineral oil, the CBD percentage in the ultimate matrix or TDD would be unchanged, but the percentages of PIB and mineral oil would change accordingly. The skilled formulator knows how to adjust mineral oil content according to the mineral oil content of the PIB adhesive starting material.

In certain embodiments, the matrix also comprises a plasticizer in addition to the PIB adhesive. Suitable plasticizers include mineral oil or silicone fluid present in an amount ranging from about 1% (w/w) to about 40% (w/w) of matrix, for example from about 10% (w/w) to about 30% (w/w). In some embodiments, the amount of plasticizer ranges from about 17% (w/w) to about 28% (w/w) of the matrix, for example about 17.2% (w/w), about 17.4% (w/w), about 17.6% (w/w), about 17.8% (w/w), about 18.0% (w/w), about 18.2% (w/w), about 18.4% (w/w), about 18.6% (w/w), about 18.8% (w/w), about 19.0% (w/w), about 19.2% (w/w), about 19.4% (w/w), about 19.6% (w/w), about 19.8% (w/w), about 20.0% (w/w), about 21.0% (w/w), about 21.2% (w/w), about 21.4% (w/w), about 21.6% (w/w), about 21.8% (w/w), or about 22.0% (w/w). Suitable mineral oils for use as plasticizers in the matrices and TDDs of the present disclosure have a kinematic viscosity of about 5 to about 30 cSt at 40° C., for example about 10.8 to about 13.6 cSt at 40° C.

Cannabidiol content. As discussed above, the matrices and TTDs of the present disclosure are advantageously formulated with a "saturated-plus-excess" concentration of CBD. The solubility of CBD in mineral oil (and by extension a PIB/mineral oil blend since PIB and mineral oil have the same solubility) is 4% (w/w). The amount of CBD in the matrix should be at least twofold, e.g., at least threefold, at least fourfold, or at least fivefold more CBD than the maximum concentration of CBD that dissolves in the plasticizer (e.g., mineral oil). The amount of CBD in the matrix can be any amount from about 10% (w/w) to about 30% (w/w) of the matrix, for example about 12.0% (w/w), about 12.5% (w/w), about 13.0% (w/w), about 13.5% (w/w), about 14.0% (w/w), about 14.5% (w/w), about 15.0% (w/w), about 15.5% (w/w), about 16.0% (w/w), about 16.5% (w/w), about 17.0% (w/w), about 17.5% (w/w), about 18.0% (w/w), about 18.5% (w/w), about 19.0% (w/w), about 19.5% (w/w), about 20.0% (w/w), or about 20.5% (w/w) of the matrix. The amount of cannabinoids other than CBD should be less than about 10% (w/w), for example less than about 1% (w/w).

CBD can be provided for the matrices and TDDs disclosed herein as either pure CBD crystals or CBD oil. Whether provided as crystal or as oil, the CBD content will be adjusted to be within the concentration ranges disclosed above. The skilled formulator knows how to calculate the weight percent of CBD in the ultimate matrix or ultimate TDD, regardless of the starting material from which the matrix or TDD is assembled.

In certain embodiments in which the CBD is provided from cannabis plant oil extract, the oil may further comprise rosins and/or terpenes that remain present after extraction. These rosins and terpenes can improve adhesion of the matrix to the skin.

Penetration enhancers. In certain embodiments, a matrix or TDD as disclosed herein may also include one or more penetration enhancers. By way of non-limiting examples, suitable penetration enhancers include DMSO, isopropyl myristate (IPM), isopropyl palmitate (IPP), oleic acid, and 1,2 propylene glycol. The amount of penetration enhancer can range from 0% (w/w) to about 10% (w/w) of the matrix.

Release liners. In certain embodiments, the TDD comprises a release liner. When the release liner is present, it will be inert to the matrix and affixed on the opposite surface of matrix from the backing layer. In certain embodiments, the release liner is a thin, occlusive polymeric film, such as a polyethylene, PET, or LDPE film, or a combination of one or more of those polymers. In ordinary use, such release liners will be 0.5-8.0 mm thick, for example 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5., 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.5, 7.0, 7.5 mm or more thick. In certain embodiments, the release liner is coated with a release agent, such as wax or silicone.

Methods of Use. The TDDs disclosed herein can be used to deliver CBD to a patient in need of CBD. In certain embodiments, the CBD is delivered into the patient's bloodstream by affixing the TDD to the patient's skin and allowing the CBD to diffuse through the skin, into the bloodstream. As noted above, CBD can be used to enhance analgesics (e.g., opioids and NSAIDs), to reverse alcohol induced brain damage, to retard progression of Parkinson's and Alzheimer's diseases, and to treat schizophrenia, social anxiety disorders, & epilepsy. Bhunia S, Kolishetti N, Arias A Y, Vashist A, Nair M. Cannabidiol for neurodegenerative disorders: A comprehensive review. Front Pharmacol. 2022 Oct. 25; 13:989717. doi: 10.3389/fphar.2022.989717. PMID: 36386183; PMCID: PMC9640911; Nona C N, Hendershot C S, Le Foll B. Effects of cannabidiol on alcohol-related outcomes: A review of preclinical and human research. Exp Clin Psychopharmacol. 2019 August; 27(4): 359-369. doi: 10.1037/pha0000272. Epub 2019 May 23. PMID: 31120285. The TDDs disclosed herein are useful for all of these utilities. Where the CBD is being administered to enhance an analgesic effect, the patient should also be administered the analgesic (e.g., the opioid or NSAID), before, during, or after the affixation of the TDD. Advantageously, the TDDs disclosed herein have higher flux and bioavailability of CBD than previous CBD patches.

The TDDs disclosed herein can be used by affixing the adhesive matrix to the skin of the patient in need of CBD treatment. The location of skin contact is not particularly limited, although most patients will prefer not to wear the TDD on the face or feet. Suitable locations for application include but are not limited to the skin of the arms (particularly above the elbow), the back, the abdomen, the thigh, the calves, and the buttocks. Where the release liner is present in the TDD, it should be removed before attempting to affix the TDD to the skin. In certain embodiments, the patient will affix a TDD to one location, and then when that TDD becomes exhausted and need to be replaced, the patient will affix the new TDD to a different location.

In certain embodiments, the TDD delivers a transdermal flux of at least 0.40 mg/cm$^2$ per 24 hours, for example at least 0.45, at least 0.50, at least 0.55, at least 0.60, at least 0.65, or at least 0.70 mg/cm$^2$ per 24 hours.

In certain embodiments, the skin contact area of the TDD is at least about 10 cm$^2$, for example at least about 15 cm$^2$, at least about 18 cm$^2$, or at least about 20 cm$^2$. At the same time, in some embodiments the skin contact area of the TDD is no more than about 50 cm$^2$, for example less than about 45 cm$^2$, less than about 40 cm$^2$, less than about 45 cm$^2$, less than about 30 cm$^2$, less than about 25 cm$^2$, or less than about 22 cm$^2$.

Once the TDD is affixed to the skin, in some aspects, the present disclosure includes a method of contacting the TDD with the skin for at least an hour, for example at least 4 hours, at least 8 hours, at least 10 hours, at least 12 hours, at least 24 hours, or at least 36 hours. During that time, the CBD will permeate across the skin and into the subject's bloodstream, thus effecting the therapeutic purpose for which the TDD is intended. In some aspects, after 24 to 36 hours of use, the methods disclosed herein include removing the TDD from the skin. In some aspects, for example, depending on the condition or disorder that the TDD was intended to treat, the TDD is replaced immediately. Alternatively, in some aspects, the method includes applying a new TDD after at least one hour, at least 2 hours, at least 8 hours, at least 12 hours, at least 24 hours, or at least 48 hours.

Methods of making. The manufacture of a TDD as disclosed herein involves four main processes: high shear mixing; low shear mixing; film casting & drying; and patch punching. The high sheer mixing can be accomplished with any of a variety of commercially available high-sheer mixers known in the industry, such as those manufactured by Ross & Son, Co. (Hauppauge, New York) or Silverson Machines, Inc. (East Longmeadow, Massachusetts).

In certain embodiments, the process includes mixing about 35 to about 70 weight parts of PIB adhesive having an average molecular weight greater than 100 kDa with about 15 to about 50 parts by weight of an oil and at least 15 parts by weight of CBD. In certain embodiments, the method begins by mixing the CBD with the oil in an organic solvent to obtain a first mixture, followed by a second step of mixing the first mixture with the PIB adhesive and stirring. In certain embodiments, the first mixing step has a higher stir rate than the second mixing step. An exemplary process description is provided in Example 1 below.

Numbered Aspects

The following numbered aspects also form part of the present disclosure.

Aspect 1. A transdermal delivery device (TDD) comprising a backing layer and a matrix, wherein the matrix comprises polyisobutylene (PIB) adhesive, an oil, and cannabidiol (CBD), wherein the matrix comprises at least threefold more CBD than a maximum concentration of CBD that dissolves in the oil, wherein the PIB adhesive has an average molecular weight greater than 100 kDa, and wherein the backing layer is inert to the matrix.

Aspect 2. The TDD of aspect 1, wherein the oil is a mineral oil with a kinematic viscosity of about 5 to about 30 cSt at 40° C., and wherein about 10% (w/w) to about 30% (w/w) of the mass of the matrix is the mineral oil.

Aspect 3. The TDD of aspect 1 or aspect 2, wherein about 35% (w/w) to about 75% (w/w) of the mass of the matrix is PIB.

Aspect 4. The TDD of any one of the preceding aspects, wherein the PIB comprises polymers with a molecular weight from about 800 kDa to about 4 MDa and polymers with a molecular weight from about 25 kDa to about 65 kDa in a ratio of about 1:2 to about 2:1.

Aspect 5. The TDD of any one of the preceding aspects, wherein the matrix comprises at least fourfold more CBD than the saturation concentration for CBD in the oil.

Aspect 6. The TDD of any one of the preceding aspects, wherein about 16% (w/w) to about 17% (w/w) of the mass of the matrix is CBD, about 55% (w/w) to about 66% (w/w) of the mass of the matrix is PIB, and about 17% (w/w) to about 28% (w/w) of the mass of the matrix is a mineral oil with a kinematic viscosity of about 10.8 to about 13.6 cSt at 40° C.

Aspect 7. The TDD of any one of the preceding aspects, further comprising a 1.0 to 5.0 mm thick polyethylene terephthalate (PET) film coated with a release agent.

Aspect 8. The TDD of any one of the preceding aspects, wherein the backing layer is a 1.0 to 5.0 mm thick low density polyethylene (LDPE) film.

Aspect 9. The TDD of any one of the preceding aspects, wherein the TDD is configured to deliver at least 0.5 mg/cm2 of CBD across skin of a human subject after adherence of the TDD to the skin for at least 24 hours.

Aspect 10. The TDD of aspect 9, wherein the TDD is configured to deliver at least 0.65 mg/cm2 of CBD across skin of a human subject after adherence of the TDD to the skin for at least 24 hours.

Aspect 11. The TDD of any one of the preceding aspects, wherein the TDD is configured to deliver at least 50% (w/w) of the CBD through a human subject's skin after adherence of the TDD to the skin for at least 12 hours.

Aspect 12. The TDD of aspect 11, wherein the TDD is configured to deliver at least 70% (w/w) of the CBD through a human subject's skin after adherence of the TDD to the skin for at least 24 hours.

Aspect 13. A TDD comprising a backing layer and a matrix comprising PIB adhesive, an oil, and at least 16% (w/w) CBD, wherein the backing layer is inert to the matrix, and wherein the TDD is configured to deliver at least 0.5 mg/cm2 of CBD across skin of a human subject after adherence of the TDD to the skin for at least 24 hours.

Aspect 14. The TDD of aspect 13, wherein the oil is a mineral oil with a kinematic viscosity of about 5 to about 30 cSt (for example, about 10.8 to about 13.6 cSt) at 40° C., and wherein about 15% (w/w) to about 50% (w/w) of the mass of the matrix is mineral oil.

Aspect 15. The TDD of aspect 13 or aspect 14, wherein about 35% (w/w) to about 70% (w/w) of the mass of the matrix is PIB.

Aspect 16. The TDD of any one of aspects 13-15, wherein the PIB comprises polymers with a molecular weight from about 800 kDa to about 4 MDa and polymers with a molecular weight from about 25 kDa to about 65 kDa in a ratio of about 1:2 to about 2:1.

Aspect 17. The TDD of any one of aspects 13-16, wherein about 15 to about 25% (w/w) of the matrix is CBD.

Aspect 18. The TDD of any one of aspects 13-17, wherein about 55% (w/w) to about 66% (w/w) of the mass of the matrix is PIB, and about 17% (w/w) to about 28% (w/w) of the mass of the matrix is mineral oil.

Aspect 19. The TDD of any one of aspects 13-18, further comprising a 1.0 to 5.0 mm thick PET film coated with a release agent.

Aspect 20. The TDD of any one of aspects 13-19, wherein the backing layer is a 1.0 to 5.0 mm thick LDPE film.

Aspect 21. The TDD of any one of aspects 13-20, wherein the TDD is configured to deliver at least 0.65 mg/cm2 of CBD across skin of a human subject after adherence of the TDD to the skin for at least 24 hours.

Aspect 22. The TDD of any one of aspects 13-21, wherein the TDD is configured to deliver at least 50% (w/w) of the CBD through a human subject's skin after adherence of the TDD to the skin for at least 12 hours.

Aspect 23. The TDD of aspect 22, wherein the TDD is configured to deliver at least 70% (w/w) of the CBD through a human subject's skin after adherence of the TDD to the skin for at least 24 hours.

Aspect 24. A method of delivering CBD to a subject, the method comprising adhering the TDD of any one of aspects 1-23 to skin of the subject for at least 8 hours.

Aspect 25. The method of aspect 24, comprising delivering CBD at a transdermal flux of at least 0.6 mg/cm2 per 24 hours to the subject.

Aspect 26. A method of treating a subject suffering from seizures, comprising adhering the TDD of any one of aspects 1-23 to skin of the subject.

Aspect 27. A method of enhancing an analgesic effect in a subject in need of pain relief, the method comprising adhering the TDD of any one of aspects 1-23 to skin of the subject, wherein the subject has been, is, or will be administered an analgesic agent.

Aspect 28. A method of making a pharmaceutical matrix, the method comprising mixing about 35 to about 70 weight parts of PIB adhesive having an average molecular weight greater than 100 kDa with about 15 to about 50 parts by weight of an oil and at least 15 parts by weight of CBD, wherein the method comprises a first mixing step of mixing the CBD with the oil in an organic solvent to obtain a first mixture, followed by a second mixing step of mixing the first mixture with the PIB adhesive and stirring, wherein the first mixing step has a higher stir rate than the second mixing step.

EXAMPLES

The invention is further described in the following examples, which do not limit the scope of the claimed invention.

Example 1 (Manufacturing). The mixing processes are described for a scale of 200 ml of the adhesive solution. In a laboratory scale high shear mixer (Silverson Machines, Inc., East Longmeadow, Massachusetts) 14.7 g of CBD, 18.5 mL of light mineral oil, and 2.5 mL of n-heptane are added and mixed at medium speed until a uniform suspension of CBD in the liquids is obtained.

200 mL of adhesive solution is added to a flask with a stir bar set to a low stirring rate on a magnetic stir plate. The uniform CBD suspension is then added to the flask and mixed until a uniform suspension of CBD and adhesive is obtained. This suspension is the casting solution which will form the matrix of the TDD once dried.

A 12 inch length of release liner is secured to a glass plate with the siliconized surface upward using adhesive tape. A casting knife (Gardco, Inc., Pompano Beach, Florida) is set to a gap of 5 mm. The casting solution is poured on the liner in front of the casting knife and a cast made. The wet film is placed in a convection oven at 80° C. for 10 minutes. A section of the backing film is laminated to the dried film using a weighted roller. The laminated film is removed from the glass plate. This is the final laminate—i.e., the matrix adhered to the backing layer.

The final laminate is punched using a 2 inch diameter arch punch. This is the assembled TDD. In a final, optional step, the assembled TDDs can be placed in pouches and the pouches sealed.

Example 2 (Material assays of TDDs). A single lot of TDDs made according to the methods disclosed herein were sent to a contract analytical lab to be assayed for contamination with pesticides, heavy metals, bacteria, fungi, mycotoxins, residual solvents, and grime. They were also assayed for presence of a variety of cannabinoids and terpenes. The results of these assays are shown in Table 1 below and in FIG. 1.

TABLE 1

| Assayed TDD content | | |
|---|---|---|
| Cannabinoid | LOD | Assay Qty. |
| D9-THC | 0.002% | 0.00 mg/g |
| CBD | 0.002% | 13.21 mg/g |
| D8-THC | 0.002% | 0.00 mg/g |
| CBGA | 0.002% | 0.00 mg/g |
| THCV | 0.002% | 0.00 mg/g |
| CBC | 0.002% | 0.00 mg/g |
| THCA | 0.002% | 0.00 mg/g |
| CBDA | 0.002% | 0.00 mg/g |
| CBG | 0.002% | 0.00 mg/g |
| CBN | 0.002% | 0.00 mg/g |
| CBDV | 0.002% | 0.00 mg/g |
| Terpene | LOD | Assay Qty. |
| Total terpineol | 0.007% | 0.00 mg/g |
| Camphene | 0.007% | 0.00 mg/g |
| β-Myrcene | 0.007% | 0.00 mg/g |
| 3-Carene | 0.007% | 0.00 mg/g |
| α-Phellandrene | 0.007% | 0.00 mg/g |
| Ocimene | 0.007% | 0.00 mg/g |
| Eucalyptol | 0.007% | 0.00 mg/g |
| Linalool | 0.007% | 0.00 mg/g |
| Fenchone | 0.007% | 0.00 mg/g |
| Isopulegol | 0.007% | 0.00 mg/g |
| Isoborneol | 0.007% | 0.00 mg/g |
| Hexhydrothymol | 0.007% | 0.00 mg/g |
| Nerol | 0.007% | 0.00 mg/g |
| Geranyl acetate | 0.007% | 0.00 mg/g |
| β-Caryophyllene | 0.007% | 0.00 mg/g |
| Valencene | 0.007% | 0.00 mg/g |
| Caryophyllene oxide | 0.007% | 0.00 mg/g |
| α-Bisabolol | 0.007% | <0.2 mg/g |
| A-Pinene | 0.007% | 0.00 mg/g |
| Sabinene | 0.007% | 0.00 mg/g |
| β-Pinene | 0.007% | 0.00 mg/g |
| α-Terpinene | 0.007% | 0.00 mg/g |
| Limonene | 0.007% | 0.00 mg/g |
| γ-Terpinene | 0.007% | 0.00 mg/g |
| Terpinolene | 0.007% | 0.00 mg/g |
| Sabinene hydrate | 0.007% | 0.00 mg/g |

TABLE 1-continued

| Assayed TDD content | | |
|---|---|---|
| Fenchyl alcohol | 0.007% | 0.00 mg/g |
| Camphor | 0.007% | 0.00 mg/g |
| Borneol | 0.013% | 0.00 mg/g |
| Geraniol | 0.007% | 0.00 mg/g |
| Pulegone | 0.007% | 0.00 mg/g |
| α-Cedrene | 0.007% | 0.00 mg/g |
| α-Humulene | 0.007% | 0.00 mg/g |
| Trans-Nerolidol | 0.007% | 0.00 mg/g |
| Cis-Nerolidol | 0.007% | <0.2 mg/g |
| Cedrol | 0.007% | <0.2 mg/g |
| Farnesene | 0.000% | <0.01 mg/g |
| Guaiol | 0.007% | 0.00 mg/g |
| Mycotoxin | LOD | Assay Qty. |
| Aflatoxin B1 | 0.002 ppm | ND |
| Aflatoxin B2 | 0.002 ppm | ND |
| Aflatoxin G1 | 0.002 ppm | ND |
| Aflatoxin G2 | 0.002 ppm | ND |
| Ochratoxin A | 0.002 ppm | ND |
| Pesticides | 0.01 ppm | ND |
| Solvents | 0.1 ppm | ND |
| Heavy Metals | LOD | Assay Qty. |
| Arsenic | 0.02 ppm | ND |
| Cadmium | 0.02 ppm | ND |
| Mercury | 0.02 ppm | ND |
| Lead | 0.05 ppm | ND |
| Microbe | | Assay Qty. |
| Escherichia coli | | ND |
| Shigella spp. | | ND |
| Salmonella spp. | | ND |
| Aspergillus flavus | | ND |
| Aspergillus fumigatus | | ND |
| Aspergillus terreus | | ND |
| Aspergillus niger | | ND |
| Foreign contaminant | LOD | Assay Qty. |
| Fifth | 1% | ND | ppm = parts per million; LOD = limit of detection; ND = not detected; Qty. = quantity Example 3 (Bioavailability). A bioavailability study in humans was conducted using the TDDs as described in Example 2 above. A batch of TDDs was assayed for CBD content and each 25 cm$^2$ TDD was determined to contain an average of 21.2 mg of CBD.

The TDDs were applied to the arms of human volunteers for a period of 24 hours. After 24 hours, the TDDs were removed and assayed for residual drug. The worn TDDs were determined to contain an average of 4.49 mg of residual CBD. This indicates delivery of 16.71 mg of CBD over 24 hours.

This corresponds to approximately 79% of the initial CBD loading. In other words, the TDDs had an apparent 79% CBD bioavailability. Additionally, this result indicates that the TDD was depleted to only 3.26% of CBD loading content by the time of removal. This residual CBD content is just below the saturation concentration of 4 percent discussed above. Therefore, it follows that the TDD was delivering CBD at the maximum driving force throughout virtually the entire 24 hour delivery period. The observed transdermal flux of 670 µg/cm$^2$-day is significantly higher, i.e., about 2.9- to 6.7-fold, than the highest CBD flux values reported in the scientific and patent literature for CBD patches, including all of the documents listed in the background section above.

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A transdermal delivery device (TDD) comprising a backing layer and a matrix, wherein the matrix comprises polyisobutylene (PIB) adhesive, an oil, and cannabidiol (CBD), wherein the matrix comprises at least threefold more CBD than a maximum concentration of CBD that dissolves in the oil, wherein the PIB adhesive has an average molecular weight greater than 100 kDa, and wherein the backing layer is inert to the matrix, wherein the oil is a mineral oil with a kinematic viscosity of about 5-30 cSt at 40° C., wherein about 10% (w/w) to about 30% (w/w) of the mass of the matrix is the mineral oil, and wherein the TDD is configured to deliver at least 0.5 mg/cm$^2$ of CBD across skin of a human subject after adherence of the TDD to the skin for at least 24 hours.

2. The TDD of claim 1, wherein about 35% (w/w) to about 75% (w/w) of the mass of the matrix is PIB.

3. The TDD of claim 2, wherein the PIB comprises polymers with a molecular weight from about 800 kDa to about 4 MDa and polymers with a molecular weight from about 25 kDa to about 65 kDa in a ratio of about 1:2 to about 2:1.

4. The TDD of claim 3, wherein the matrix comprises at least fourfold more CBD than the saturation concentration for CBD in the oil.

5. The TDD of claim 4, wherein about 16-17% (w/w) of the mass of the matrix is CBD, about 55-66% (w/w) of the mass of the matrix is PIB, and about 17-28% (w/w) of the mass of the matrix is a mineral oil with a kinematic viscosity of about 10.8-13.6 cSt at 40° C.

6. The TDD of claim 1, further comprising a 1.0-5.0 mm thick polyethylene terephthalate (PET) film coated with a release agent.

7. The TDD of claim 1, wherein the backing layer is a 1.0-5.0 mm thick low density polyethylene (LDPE) film.

8. The TDD of claim 1, wherein the TDD is configured to deliver at least 0.65 mg/cm$^2$ of CBD across skin of a human subject after adherence of the TDD to the skin for at least 24 hours.

9. The TDD of claim 1, wherein the TDD is configured to deliver at least 50% (w/w) of the CBD through a human subject's skin after adherence of the TDD to the skin for at least 12 hours.

10. The TDD of claim 9, wherein the TDD is configured to deliver at least 70% (w/w) of the CBD through a human subject's skin after adherence of the TDD to the skin for at least 24 hours.

11. A TDD comprising a backing layer and a matrix comprising PIB adhesive, an oil, and at least 16% (w/w) CBD, wherein the backing layer is inert to the matrix, and wherein the TDD is configured to deliver at least 0.5 mg/cm$^2$ of CBD across skin of a human subject after adherence of the TDD to the skin for at least 24 hours, wherein the oil is a mineral oil with a kinematic viscosity of about 5-30 cSt at 40° C., and wherein about 15% (w/w) to about 50% (w/w) of the mass of the matrix is mineral oil.

12. The TDD of claim 11, wherein about 35% (w/w) to about 70% (w/w) of the mass of the matrix is PIB.

13. The TDD of claim 12, wherein the PIB comprises polymers with a molecular weight from about 800 kDa to about 4 MDa and polymers with a molecular weight from about 25 kDa to about 65 kDa in a ratio of about 1:2 to about 2:1.

14. The TDD of claim 13, wherein about 15-25% (w/w) of the matrix is CBD.

15. The TDD of claim 14, wherein about 55-66% (w/w) of the mass of the matrix is PIB, and about 17-28% (w/w) of the mass of the matrix is mineral oil.

16. The TDD of claim 15, further comprising a 1.0-5.0 mm thick PET film coated with a release agent.

17. The TDD of claim 11, wherein the backing layer is a 1.0-5.0 mm thick LDPE film.

18. The TDD of claim 11, wherein the TDD is configured to deliver at least 0.65 mg/cm$^2$ of CBD across skin of a human subject after adherence of the TDD to the skin for at least 24 hours.

19. The TDD of claim 11, wherein the TDD is configured to deliver at least 50% (w/w) of the CBD through a human subject's skin after adherence of the TDD to the skin for at least 12 hours.

20. The TDD of claim 19, wherein the TDD is configured to deliver at least 70% (w/w) of the CBD through a human subject's skin after adherence of the TDD to the skin for at least 24 hours.

21. A method of delivering CBD to a subject, the method comprising adhering the TDD of claim 1 to skin of the subject for at least 8 hours.

22. The method of claim 21, comprising delivering CBD at a transdermal flux of at least 0.6 mg/cm$^2$ per 24 hours to the subject.

23. A method of delivering CBD to a subject, the method comprising adhering the TDD of claim 11 to skin of the subject for at least 8 hours.

24. The method of claim 23, comprising delivering CBD at a transdermal flux of at least 0.6 mg/cm$^2$ per 24 hours to the subject.

25. A method of treating a subject suffering from seizures, comprising adhering the TDD of claim 1 to skin of the subject.

26. A method of enhancing an analgesic effect in a subject in need of pain relief, the method comprising adhering the TDD of claim 1 to skin of the subject, wherein the subject has been, is, or will be administered an analgesic agent.

* * * * *